United States Patent
Aoki et al.

(10) Patent No.: US 10,072,594 B2
(45) Date of Patent: Sep. 11, 2018

(54) EXHAUST SENSOR (71) Applicant: TOYOTA JIDOSHA KABUSHIKI KAISHA, Toyota-shi, Aichi-ken (JP)

(72) Inventors: Keiichiro Aoki, Shizuoka-ken (JP); Yoshihisa Serizawa, Shizuoka-ken (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/637,500

(22) Filed: Jun. 29, 2017

(65) Prior Publication Data
US 2018/0003119 A1 Jan. 4, 2018

(30) Foreign Application Priority Data

Jul. 4, 2016 (JP) .................. 2016-132346

(51) Int. Cl.
*G01M 15/10* (2006.01)
*F02D 41/14* (2006.01)
(Continued)

(52) U.S. Cl.
CPC ....... *F02D 41/1495* (2013.01); *F02D 41/123* (2013.01); *F02D 41/1455* (2013.01); *G01M 15/104* (2013.01); *G01N 33/0006* (2013.01)

(58) Field of Classification Search
CPC ............. F02D 41/1495; F02D 41/1455; F02D 41/1496; F02D 41/146; F02D 41/123; G01N 33/0006; G01N 33/0037; G01N 33/0054; G01N 27/4075; G01N 27/4074; G01N 27/4071; G01N 27/4072; G01M 15/104

See application file for complete search history.

(56) References Cited

U.S. PATENT DOCUMENTS 6,309,536 B1 * 10/2001 Inagaki .............. B01D 53/9495
204/408
2003/0140617 A1 * 7/2003 Yasui .................. F02D 41/1403
60/276

(Continued)

FOREIGN PATENT DOCUMENTS

JP  2001-133429 A   5/2001
JP  2009-014706 A   1/2009
(Continued)

*Primary Examiner* — Lindsay Low
*Assistant Examiner* — George Jin
(74) *Attorney, Agent, or Firm* — Hunton Andrews Kurth LLP (57) ABSTRACT

An exhaust sensor 1 comprises a sensor cell 51, a voltage application circuit 61, a current detection circuit 62 and a concentration calculating part 80a. The current detection circuit detects a first current flowing through the sensor cell when fuel cut control is being performed in the internal combustion engine and a predetermined voltage is applied from the voltage application circuit to the sensor cell, and detect a second current flowing through the sensor cell when normal control is being performed in the internal combustion engine and the predetermined voltage is applied from the voltage application circuit to the sensor cell. The concentration calculating part is configured to calculate the concentration higher with respect to the second current when the first current is relatively low compared with when the first current is relatively high.

10 Claims, 9 Drawing Sheets (51) Int. Cl.
*G01N 33/00* (2006.01)
*F02D 41/12* (2006.01)

(56) References Cited

U.S. PATENT DOCUMENTS

| | | | |
|---|---|---|---|
| 2005/0284132 A1* | 12/2005 | Makki | F01N 3/0814 60/285 |
| 2005/0284133 A1* | 12/2005 | Kerns | F01N 11/007 60/285 |
| 2009/0218220 A1 | 9/2009 | Matter et al. | |
| 2014/0331649 A1* | 11/2014 | Tanaka | F02D 41/0235 60/277 |
| 2014/0331652 A1* | 11/2014 | Tanaka | F01N 11/007 60/285 |
| 2015/0013441 A1* | 1/2015 | Aoki | G01N 27/4065 73/114.71 |
| 2016/0123920 A1 | 5/2016 | Ueda et al. | |

FOREIGN PATENT DOCUMENTS

| | | |
|---|---|---|
| JP | 2011-513735 A | 4/2011 |
| JP | 2014-171919 A | 9/2014 |

\* cited by examiner

EXHAUST SENSOR

CROSS-REFERENCE TO RELATED APPLICATION

The present application claims priority to Japanese Patent Application No. 2016-132346 filed on Jul. 4, 2016, which is incorporated herein by reference in its entirety.

TECHNICAL FIELD

The present invention relates to an exhaust sensor.

BACKGROUND ART

In the past, in order to detect the concentration of a specific component in exhaust gas flowing through an exhaust passage of an internal combustion engine, it has been known to arrange an exhaust sensor in the exhaust passage of the internal combustion engine. The exhaust sensor is, for example, a nitrogen oxide sensor ($NO_X$ sensor) detecting the concentration of nitrogen oxide in the exhaust gas (for example, see PLTs 1 to 4).

An exhaust sensor is provided with a sensor cell having a solid electrolyte layer, a positive electrode and negative electrode. In the exhaust sensor, the current flowing through the sensor cell when a predetermined voltage is applied to the sensor cell is detected as the output of the sensor cell. Based on the detected output, the concentration of a specific component in the exhaust gas is calculated. For example, the concentration is calculated using a map showing the concentration as a function of the output of the sensor cell. In this map, the higher the output of the sensor cell, the higher the concentration.

CITATION LIST

Patent Literature

PLT 1: Japanese Patent Publication No. 2014-171919A
PLT 2: Japanese Patent Publication No. 2011-513735A
PLT 3: Japanese Patent Publication No. 2009-014706A
PLT 4: Japanese Patent Publication No. 2001-133429A

SUMMARY OF INVENTION

Technical Problem

However, if an exhaust sensor is used over a long period of time, due to deterioration along with the elapse of time, the characteristics of the electrodes, etc., of the sensor cell change and the output of the sensor cell falls. If the concentration is calculated based on the fallen output, the concentration is calculated lower than the actual concentration and the precision of detection of the concentration falls.

Therefore, an object of the present invention is to provide an exhaust sensor able to suppress a drop in precision of detection of concentration due to a drop in output of a sensor cell caused by deterioration along with the elapse of time.

Solution to Problem

In order to solve the above problem, in a first aspect, there is provided an exhaust sensor detecting a concentration of a specific component in exhaust gas flowing through an exhaust passage of an internal combustion engine, comprising: a sensor cell having a solid electrolyte layer having an oxide ion conductivity, a first electrode arranged on one surface of the solid electrolyte layer so as to be exposed to the exhaust gas and comprised of a perovskite-type oxide, and a second electrode arranged on the other surface of the solid electrolyte layer so as to be exposed to a reference gas; a voltage application circuit applying voltage to the sensor cell so that a potential of the second electrode becomes higher than a potential of the first electrode, a current detection circuit detecting a current flowing through the sensor cell; and a concentration calculating part configured to calculate the concentration based on a current detected by the current detection circuit, wherein the current detection circuit detects a first current flowing through the sensor cell when fuel cut control where fuel stops being fed to combustion chambers of the internal combustion engine is being performed in the internal combustion engine and a predetermined voltage is applied from the voltage application circuit to the sensor cell, and detects a second current flowing through the sensor cell when normal control where fuel is being fed to the combustion chambers is being performed in the internal combustion engine and the predetermined voltage is applied from the voltage application circuit to the sensor cell, and the concentration calculating part is configured to calculate the concentration higher with respect to the second current when the first current is relatively low compared with when the first current is relatively high.

In a second aspect, the concentration calculating part is configured to calculate the concentration based on a ratio of the first current and the second current, in the first aspect.

In a third aspect, the concentration calculating part is configured to correct the second current based on a ratio of an initial value of the first current and a current value of the first current and calculates the concentration based on the corrected second current, in the first aspect.

In a forth aspect, the initial value of the first current is predetermined and is an average value of initial values of first currents at a plurality of the exhaust sensors, in the third aspect.

In a fifth aspect, the initial value of the first current is an average value of first currents first detected a predetermined number of times by the current detection circuit after the exhaust sensor is mounted in the internal combustion engine, in the third aspect.

In a sixth aspect, the exhaust sensor is a one-cell type nitrogen oxide sensor detecting a concentration of nitrogen oxide in exhaust gas, in any one of the first to fifth aspects.

Advantageous Effects of Invention

According to the present invention, there is provided an exhaust sensor able to suppress a drop in precision of detection of concentration due to a drop in output of a sensor cell caused by deterioration along with the elapse of time.

DESCRIPTION OF EMBODIMENTS

Below, referring to the drawings, embodiments of the present invention will be explained in detail. Note that, in the following explanation, similar components will be assigned the same reference notations.

First Embodiment

First, referring to FIG. 1 to FIG. 8, a first embodiment of the present invention will be explained.

<Explanation of Internal Combustion Engine as Whole>

Figure 1:
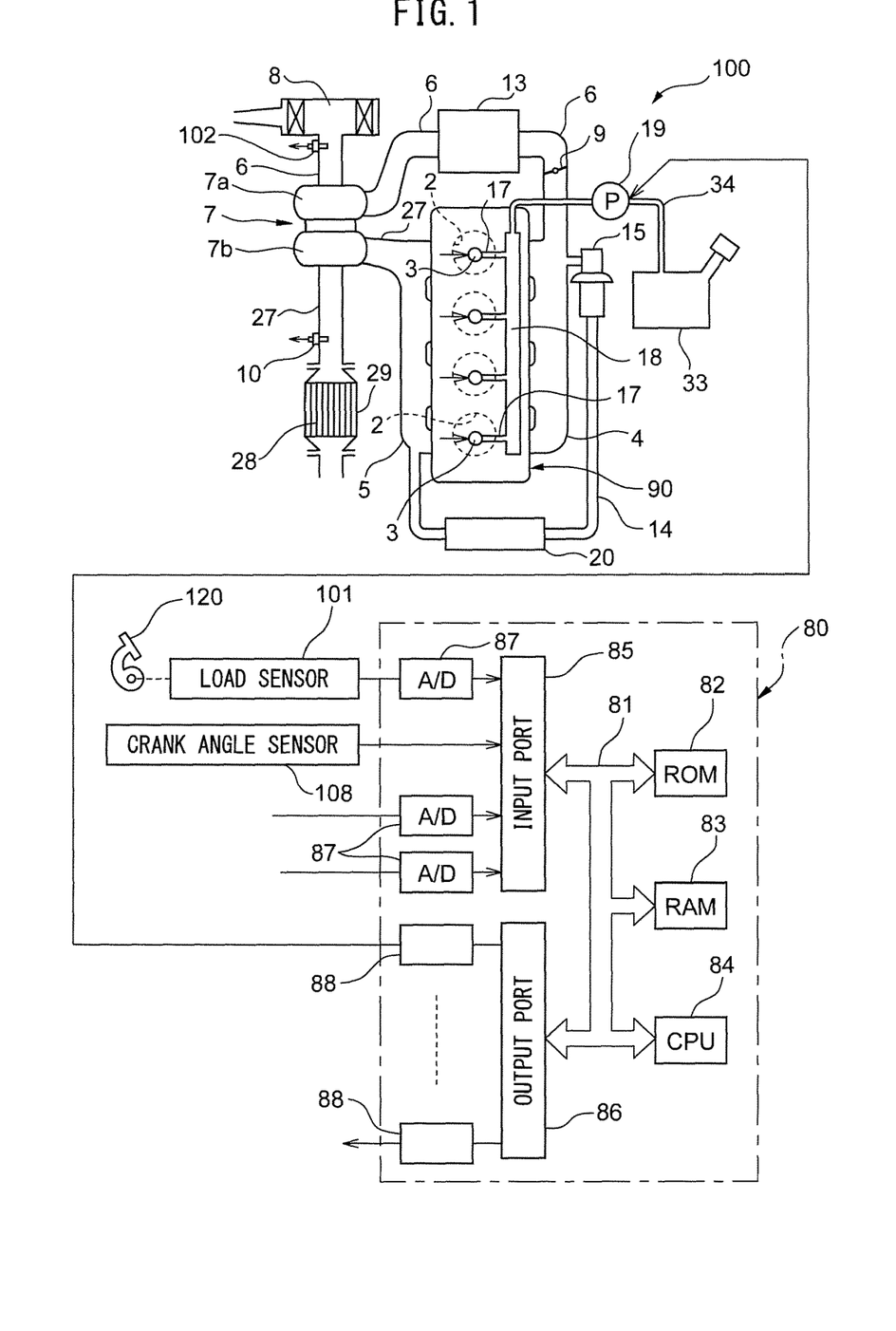
FIG. 1 is a view schematically showing an internal combustion engine to which an exhaust sensor according to a first embodiment of the present invention is applied.

FIG. 1 is a view schematically showing an internal combustion engine 100 in which an exhaust sensor according to the first embodiment of the present invention is applied. The internal combustion engine 1 shown in FIG. 1 is a compression ignition type internal combustion engine (diesel engine). The internal combustion engine 100 is for example mounted in a vehicle.

Referring to FIG. 1, the internal combustion engine 100 is provided with an engine body 90, a combustion chamber 2 of each cylinder, an electronically controlled fuel injector 3 injecting fuel into each combustion chamber 2, an intake manifold 4, and an exhaust manifold 5. The intake manifold 4 is connected through an intake pipe 6 to an outlet of a compressor 7a of a turbocharger 7. The inlet of the compressor 7a is connected through the intake pipe 6 to an air cleaner 8. Inside the intake pipe 6, a throttle valve 9 driven by a step motor is arranged. Furthermore, around the intake pipe 6, a cooling device 13 for cooling the intake air flowing through the inside of the intake pipe 6 is arranged. In the internal combustion engine 100 shown in FIG. 1, engine cooling water is guided to the inside of the cooling device 13 and cools the intake air. The intake manifold 4 and intake pipe 6 form an intake passage guiding air to the inside of each combustion chamber 2.

On the other hand, the exhaust manifold 5 is connected through an exhaust pipe 27 to an inlet of a turbine 7b of the turbocharger 7. The outlet of the turbine 7b is connected through the exhaust pipe 27 to a casing 29 housing an exhaust purification catalyst 28. The exhaust manifold 5 and exhaust pipe 27 form an exhaust passage discharging exhaust gas generated by combustion of the air-fuel mixture in each combustion chamber 2. The exhaust purification catalyst 28 is, for example, a selective catalytic reduction type $NO_X$ reduction catalyst (SCR catalyst) or an $NO_X$ storage and reduction catalyst for removing the $NO_X$ in the exhaust gas by reduction. Further, inside the exhaust passage, to reduce particulate matter (PM) in the exhaust gas, an oxidation catalyst, diesel particulate filter (DPF), etc. may be arranged.

The exhaust manifold 5 and the intake manifold 4 are connected through an exhaust gas recirculation (below, referred to as "EGR") passage 14. Inside the EGR passage 14, an electronically controlled EGR control valve 15 is arranged. Further, around the EGR passage 14, an EGR cooling device 20 is arranged for cooling the EGR gas flowing through the inside of the EGR passage 14. In the embodiment shown in FIG. 1, the engine cooling water is guided to the inside of the EGR cooling device 20 and cools the EGR gas.

The fuel is supplied by an electronically controlled variable discharge fuel pump 19 from a fuel tank 33 through a fuel pipe 34 to the inside of a common rail 18. The fuel supplied to the inside of the common rail 18 is supplied through the individual fuel supply pipes 17 to the individual fuel injectors 3.

The various control routines of the internal combustion engine 100 are performed by the electronic control unit (ECU) 80. The ECU 80 is comprised of a digital computer provided with components connected to each other through a bidirectional bus 81 such as a ROM (read only memory) 82, RAM (random access memory) 83, CPU (microprocessor) 84, input port 85, and output port 86. Outputs of a load sensor 101 and an air-flow meter 102 are input through corresponding AD converters 87 to the input port 85. On the other hand, the output port 86 is connected through corresponding drive circuits 88 to the fuel injectors 3, throttle valve drive step motor, EGR control valve 15, and fuel pump 19.

The load sensor 101 generates an output voltage proportional to an amount of depression of an accelerator pedal 120. Therefore, the load sensor 101 detects the engine load. The air-flow meter 102 is arranged inside the intake passage between the air cleaner 8 and compressor 7a and detects the amount of air flowing through the inside of the intake pipe 6. Furthermore, a crank angle sensor 108 generating an output pulse every time the crankshaft rotates by for example 15° is connected to the input port 85. The crank angle sensor 108 5 s used to detect the engine speed.

Note that, the internal combustion engine 100 may be a spark ignition type internal combustion engine with spark plugs arranged in the combustion chambers. Further, specific configurations of the internal combustion engine 100 such as the cylinder array, configuration of the intake and exhaust systems, and presence or absence of a turbocharger may differ from the configuration shown in FIG. 1.

<Explanation of Exhaust Sensor>

Below, referring to FIG. 1 to FIG. 4, an exhaust sensor according to the first embodiment of the present invention will be explained. In this embodiment, the exhaust sensor is a nitrogen oxide sensor ($NO_X$ sensor) 1 detecting the nitrogen oxide ($NO_X$) in exhaust gas flowing through the exhaust passage of the internal combustion engine 100.

Figure 2:
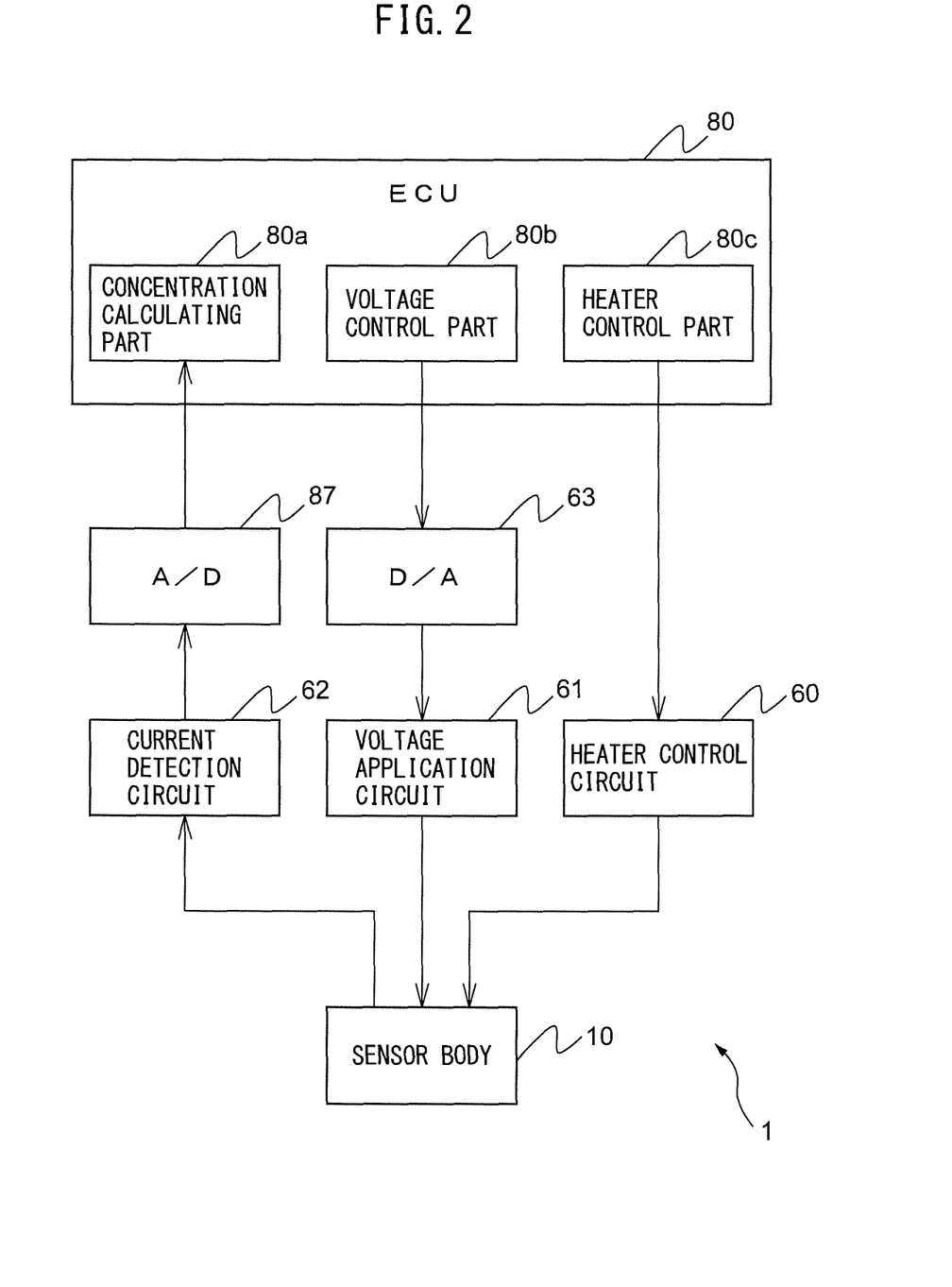
FIG. 2 is a block diagram schematically showing the configuration of an $NO_X$ sensor.

FIG. 2 is a schematic block diagram showing the configuration of the $NO_X$ sensor 1. As shown in FIG. 2, the $NO_X$ sensor 1 is provided with a sensor body 10, heater control circuit 60, voltage application circuit 61, current detection circuit 62, concentration calculating part 80a, voltage control part 80b, and heater control part 80c. The heater control circuit 60, voltage application circuit 61, and current detection circuit 62 are connected to the sensor body 10. Further, the $NO_X$ sensor 1 is further provided with a DA converter 63 connected to the voltage control part 80b and voltage application circuit 61, and an AD converter 87 connected to the concentration calculating part 80a and current detection circuit 62. In the present embodiment, the concentration calculating part 80*a*, voltage control part 80*b*, and heater control part 80*c* are parts of the ECU 80.

As shown in FIG. 1, the sensor body 10 of the $NO_X$ sensor 1 is arranged in the exhaust passage of the internal combustion engine 100 between the turbine 7*b* and exhaust purification catalyst 28. In other words, the sensor body 10 is arranged in the exhaust passage at the upstream side of the exhaust purification catalyst 28 in the direction of flow of exhaust. Note that the sensor body 10 may be arranged at another position in the exhaust passage, for example, at the downstream side of the exhaust purification catalyst 28 in the direction of flow of exhaust.

Figure 3:
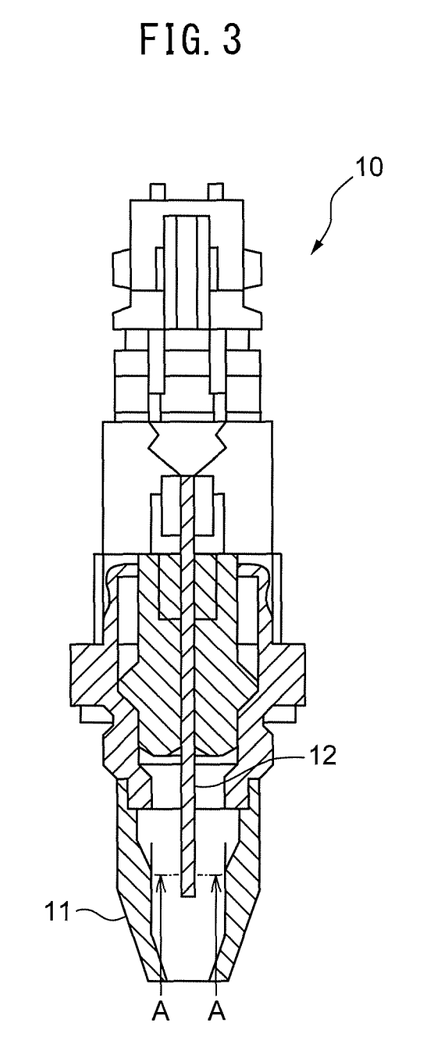
FIG. 3 is an enlarged view of a sensor body.

Below, referring to FIG. 3 and FIG. 4, the configuration of the sensor body 10 will be explained. FIG. 3 is an enlarged view of the sensor body 10. In FIG. 3, the front end side of the sensor body 10 is shown by a cross-sectional view. The sensor body 10 is fastened to the exhaust pipe 27 in the state with the front end part 11 inserted inside the exhaust pipe 27. The sensor body 10 is provided with a sensor element 12 having a plate-like shape at its inside.

Figure 4:
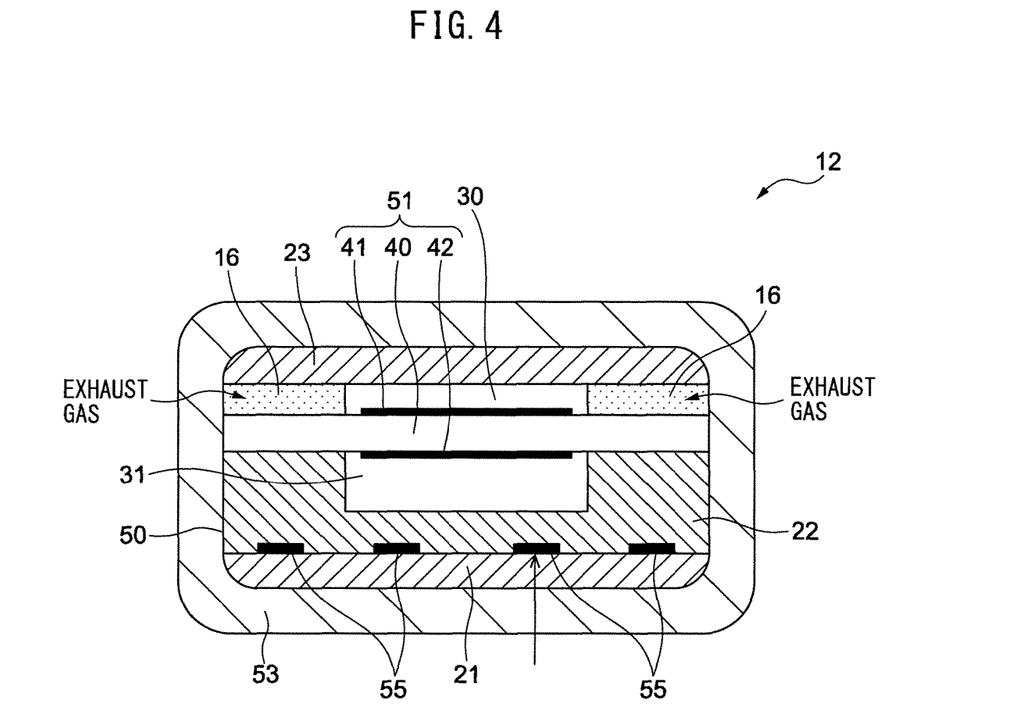
FIG. 4 is a cross-sectional view of the sensor body along the line A-A of FIG. 3.

FIG. 4 is a cross-sectional view of a sensor element 12 of the sensor body 10 along the line A-A of FIG. 3. As shown in FIG. 4, the sensor element 12 of the air-fuel ratio sensor 10 is provided with an element body 50 provided with a sensor cell 51 and a protective layer 53 formed on the outer surface of the element body 50.

The element body 50 is provided with a measured gas chamber 30 and a reference gas chamber 31. When the sensor body 10 is arranged in the exhaust passage of the internal combustion engine 100, exhaust gas flowing through the exhaust passage is introduced into the measured gas chamber 30 as the measured gas. Reference gas is introduced into the reference gas chamber 31. The reference gas is for example the atmosphere. In this case, the reference gas chamber 31 is opened to the atmosphere.

The sensor element 12 has a laminate type structure comprised of a plurality of layers laminated together. The element body 50 is provided with a solid electrolyte layer 40, diffusion regulating layer 16, first barrier layer 21, second barrier layer 22, and third barrier layer 23. The solid electrolyte layer 40 is a thin plate member having oxide ion conductivity. The solid electrolyte layer 40 is, for example, a sintered body of $ZrO_2$ (zirconia), $HfO_2$, $ThO_2$, $Bi_2O_3$, etc. to which CaO, MgO, $Y_2O_3$, $Yb_2O_3$, etc. is added as a stabilizer. The diffusion regulating layer 16 is a thin plate member having gas permeability. The diffusion regulating layer 16 is, for example, comprised of alumina, magnesia, silica, spinel, mullite, or other porous ceramic. The barrier layers 21 to 23 are gas barrier type thin sheet members, and, for example, include alumina.

The layers of the element body 50 are comprised of, from the bottom of FIG. 3, the first barrier layer 21, second barrier layer 22, solid electrolyte layer 40, diffusion regulating layer 16, and third barrier layer 23 stacked in that order. The measured gas chamber 30 is formed and defined by the solid electrolyte layer 40, diffusion regulating layer 16, and third barrier layer 23. The exhaust gas passes through the protective layer 53 and diffusion regulating layer 16 and is introduced to the inside of the measured gas chamber 30. The diffusion regulating layer 16 regulates the diffusion of the measured gas. Note that, the measured gas chamber 30 may be configured in any form so long as adjoining the solid electrolyte layer 40 and having the measured gas introduced into it.

The reference gas chamber 31 is formed and defined by the solid electrolyte layer 40 and the second barrier layer 22. Note that, the reference gas chamber 31 may be configured in any form so long as adjoining the solid electrolyte layer 40 and having the reference gas flow into it.

The sensor cell 51 is an electrochemical cell having a solid electrolyte layer 40, first electrode 41, and second electrode 42. The first electrode 41 is arranged on the surface of the solid electrolyte layer 40 on the measured gas chamber 30 side so that it is exposed to the measured gas of the measured gas chamber 30. On the other hand, the second electrode 42 is arranged on the surface of the solid electrolyte layer 40 on the reference gas chamber 31 side so that it is exposed to the reference gas inside the reference gas chamber 31. The first electrode 41 and the second electrode 42 are arranged so as to face each other across the solid electrolyte layer 40.

The first electrode 41 is comprised of a perovskite type oxide. The first electrode 41 comprised of the perovskite type oxide has the characteristic of selectively reducing and decomposing $NO_X$ in the presence of oxygen. A perovskite type oxide is, for example, $(La_{1-x}Sr_x)(CO_{1-y}Fe_y)O_{3-\delta}$ (LSCF). Due to the configuration of the first electrode 41, it is possible to detect the $NO_X$ concentration in measured gas using only the sensor cell 51 without removing the oxygen in the measured gas by a pump cell etc. Therefore, the $NO_X$ sensor 1 is a one-cell type $NO_X$ sensor in which only a single electrochemical cell is provided. In a one-cell type sensor, it is possible to increase the area of the electrode compared with a sensor in which two or more electrochemical cells are provided, so the sensor output is increased and in turn the precision of detection of the concentration is raised.

Further, the second electrode 42 is comprised of platinum (Pt). For example, the second electrode 42 is a porous cermet electrode including Pt as its main component. However, the material forming the second electrode 42 is not necessarily limited to the above material. It may be any material so long as making oxide ions move between the first electrode 41 and second electrode 42 when a predetermined voltage is applied between the first electrode 41 and the second electrode 42.

The protective layer 53 is formed on the outer surface of the element body 50 so as to cover the entire outer surface of the element body 50. The protective layer 53 has a gas permeability and is comprised of alumina, titania, zirconia, silicon carbide, silicon nitride, zinc oxide, and other porous ceramic.

The sensor element 12 is further provided with a heater 55. In the present embodiment, the heater 55, as shown in FIG. 4, is arranged between the first barrier layer 21 and the second barrier layer 22. The heater 55 is, for example, a thin plate member of cermet containing platinum (Pt) and a ceramic (for example, alumina) and is a heat generating element generating heat by conduction of current. The heater 55 heats the element body 50 and the protective layer 53. The heater control part 80*c* controls the power supplied to the heater 55 through the heater control circuit 60 so that the temperature of the sensor cell 51 becomes the activation temperature or more.

The first electrode 41 and second electrode 42 of the sensor cell 51 are connected to the voltage application circuit 61. The voltage application circuit 61 applies voltage to the sensor cell 51 so that the potential of the second electrode 42 becomes higher than the potential of the first electrode 41. Therefore, the first electrode 41 functions as a negative electrode while the second electrode 42 functions as a positive electrode. The voltage control part 80*b* inputs a voltage control signal through the DA converter 63 to the voltage application circuit 61 and controls the voltage applied from the voltage application circuit 61 to the sensor cell 51.

The current detection circuit 62 detects the current flowing through the sensor cell 51 as the output of the sensor cell 51. More specifically, the current detection circuit 62 detects the interelectrode current flowing between the first electrode 41 and the second electrode 42 (that is, the current flowing through the inside of the solid electrolyte layer 40). The output of the current detection circuit 62 is input through the AD converter 87 to the concentration calculating part 80a. Therefore, the concentration calculating part 80a can obtain the current detected by the current detection circuit 62 from the current detection circuit 62.

Note that, the specific configuration of the sensor element 12 may differ from the configuration shown in FIG. 4. For example, the sensor element 12 may have a cup-shaped structure.

<Calculation of $NO_X$ Concentration>

The concentration calculating part 80a calculates the $NO_X$ concentration in the exhaust gas based on the current detected by the current detection circuit 62 when a predetermined voltage is applied from the voltage application circuit 61 to the sensor cell 51. However, if the $NO_X$ sensor 1 is used over a long period of time, due to deterioration along with the elapse of time, the characteristics of the first electrode 41, etc., of the sensor cell 51 change and the output of the sensor cell 51 falls.

Figure 5:
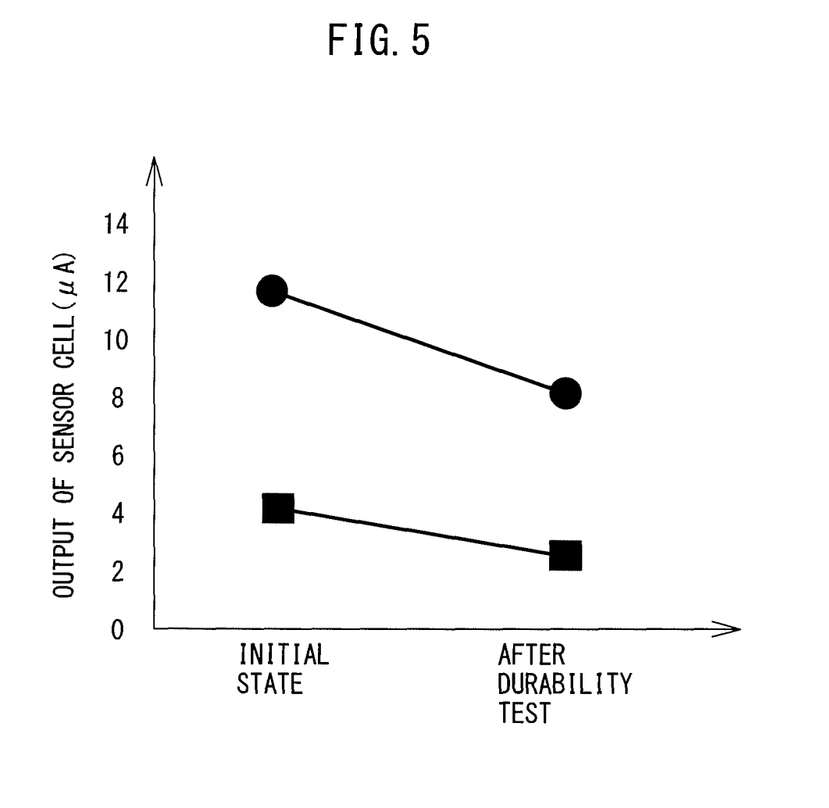
FIG. 5 is a graph showing an output of a sensor cell before and after a durability test.

FIG. 5 is a graph showing the output of the sensor cell 51 before and after a durability test. In the durability test, the sensor body 10 is exposed to an exhaust gas leaner than the stoichiometric air-fuel ratio for several hundred hours. The circle marks in the figure show the data when the exhaust gas including concentration 500 ppm NO is the measured gas. As shown in FIG. 5, the output of the sensor cell 51 after the durability test is lower than the output of the sensor cell 51 in the initial state. That is, deterioration along with the elapse of time causes the output of the sensor cell 51 to fall. If the $NO_X$ concentration is calculated based on the fallen output of the sensor cell 51, the $NO_X$ concentration will be calculated lower than the actual $NO_X$ concentration (500 ppm) and the precision of detection of the $NO_X$ concentration will fall.

On the other hand, the square marks in the figure show the data when air is the measured gas. As explained above, the first electrode 41 comprised of a perovskite type oxide has the characteristic of selectively reducing and decomposing $NO_X$ in the presence of oxygen. However, at the first electrode 41, oxygen is also slightly decomposed by reduction, so a decomposition current of oxygen flows through the sensor cell 51. The decomposition current of oxygen is smaller than the decomposition current of $NO_X$.

As shown in FIG. 5, when air is the measured gas as well, the output of the sensor cell 51 after the durability test becomes lower than the output of the sensor cell 51 in the initial state. The inventors of the present application discovered that the degree of drop in output of the sensor cell 51 when exhaust gas including $NO_X$ is the measured gas and the degree of drop in output of the sensor cell 51 when air is the measured gas become substantially equal. In other words, the inventors of the present application discovered that even if the $NO_X$ sensor 1 is used for a long period of time, the $NO_X$ selectivity of the $NO_X$ sensor 1 does not substantially change.

In this Description, the $NO_X$ selectivity SP is expressed by the following formula:

$$SP = Inox/(Inox + Iair) \times 100 \quad (1)$$

where, Inox is the sensor output when exhaust gas containing a predetermined concentration of $NO_X$ is the measured gas, while Iair is the sensor output when air is the measured gas.

Figure 6:
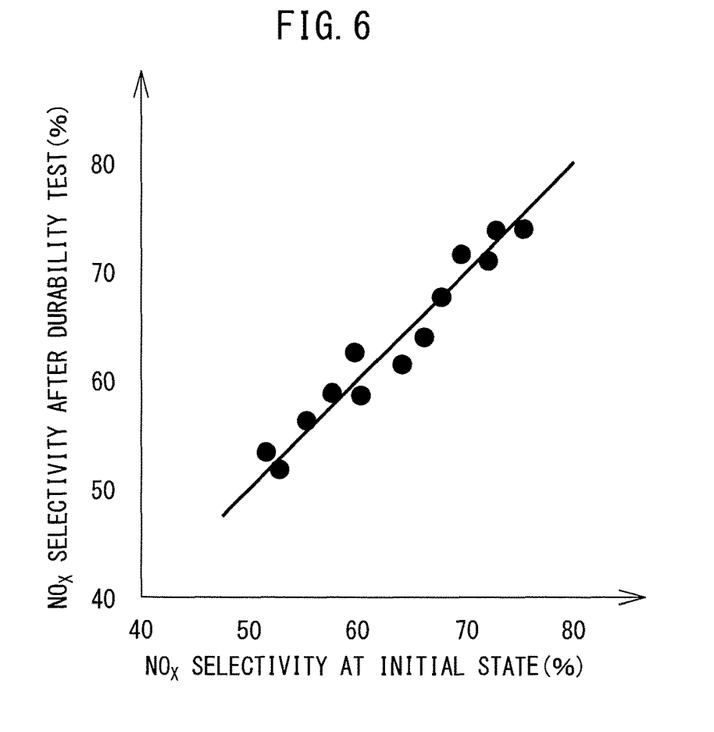
FIG. 6 is a graph showing a relationship between an $NO_X$ selectivity in an initial state of the $NO_X$ sensor and an $NO_X$ selectivity after a durability test.

FIG. 6 is a graph showing a relationship between the $NO_X$ selectivity in the initial state of the $NO_X$ sensor 1 and the $NO_X$ selectivity after the durability test. In this example, the $NO_X$ concentration is 500 ppm. As will be understood from FIG. 6, the $NO_X$ selectivity of the $NO_X$ sensor 1 does not substantially change before and after the durability test. The specific principle by which this phenomenon occurs is not necessarily clear, but it is believed to occur due to the following such mechanism.

The $NO_X$ selectivity of the $NO_X$ sensor 1 is a characteristic expressed by the crystal structure and composition of the first electrode 41 and does not depend on the thickness, area, and number of active sites of the first electrode 41. The first electrode 41 is fired at a 1100° C. or more high temperature (for example, 1200° C.), so even if the first electrode 41 is exposed to high temperature exhaust gas for a long period of time, the crystal structure and composition of the first electrode 41 will not change. Therefore, even if the $NO_X$ sensor 1 is used for a long period of time, it is believed that the $NO_X$ selectivity of the $NO_X$ sensor 1 will not change.

On the other hand, the thickness, area, and number of active sites of the first electrode 41 affect the output of the sensor cell 51. Further, if the first electrode 41 is exposed to high temperature exhaust gas for a long time, due to thermal aggregation etc., the thickness, area, and number of active sites of the first electrode 41 change. For this reason, if the $NO_X$ sensor 1 is used for a long time, it is believed that the output of the sensor cell 51 will fall.

According to the above new discovery, by detecting the output of the sensor cell 51 when air is the measured gas, it is possible to estimate the degree of deterioration of the $NO_X$ sensor 1. Further, by correcting the sensor output when exhaust gas containing $NO_X$ is the measured gas based on the degree of deterioration of the $NO_X$ sensor 1, it is possible to suppress a drop in precision of detection of the $NO_X$ concentration.

Therefore, in the present embodiment, the $NO_X$ concentration in the measured gas is calculated as explained below. The current detection circuit 62 detects the first current flowing through the sensor cell 51 when fuel cut control where fuel is stopped being fed to the combustion chambers 2 of the internal combustion engine 100 is performed in the internal combustion engine 100 and a predetermined voltage is applied from the voltage application circuit 61 to the sensor cell 51. When fuel cut control is being performed in the internal combustion engine 100, air is introduced into the measured gas chamber 30. For this reason, by detecting the first current, it is possible to detect the output of the sensor cell 51 when air is the measured gas. Further, the current detection circuit 62 detects the second current flowing through the sensor cell 51 when normal control where fuel is fed to the combustion chambers 2 is performed in the internal combustion engine 100 and the above predetermined voltage is applied from the voltage application circuit 61 to the sensor cell 51.

The concentration calculating part 80a calculates the $NO_X$ concentration higher with respect to the second current when the first current is relatively low compared with when the first current is relatively high. As a result, the $NO_X$ concentration is calculated considering the drop in output of the sensor cell 51. For this reason, the $NO_X$ sensor 1 can suppress a drop in the precision of detection of the $NO_X$ concentration due to the drop in output of the sensor cell 51 caused by deterioration along with the elapse of time.

In particular, in the present embodiment, the concentration calculating part 80a corrects the second current based on the ratio of the initial value of the first current and the current value of the first current, and calculates the $NO_X$ concentration based on the corrected second current. Specifically, the second current is corrected as follows:

$$I2ac = I2bc \times I1i/I1c \qquad (2)$$

where, I2*ac* is the corrected second current, I2*bc* is the second current before correction, I1*i* is the initial value of the first current, and I1*c* is the current value of the first current.

The value of the initial value I1*i* of the first current divided by the current value I1*c* of the first current expresses the degree of drop from the initial value of the first current. The higher this value, the greater the degree of drop from the initial value of the first current. The initial value I1*i* of the first current is, for example, the average value of the initial values of the first currents in a plurality of $NO_X$ sensors 1 and is determined in advance by experiments. In this case, the initial value I1*i* of the first current is stored in advance in the ROM 82 of the ECU 80. Further, the current value I1*c* of the first current is detected by the current detection circuit 62 before the second current is detected so as to detect the $NO_X$ concentration.

Figure 7:
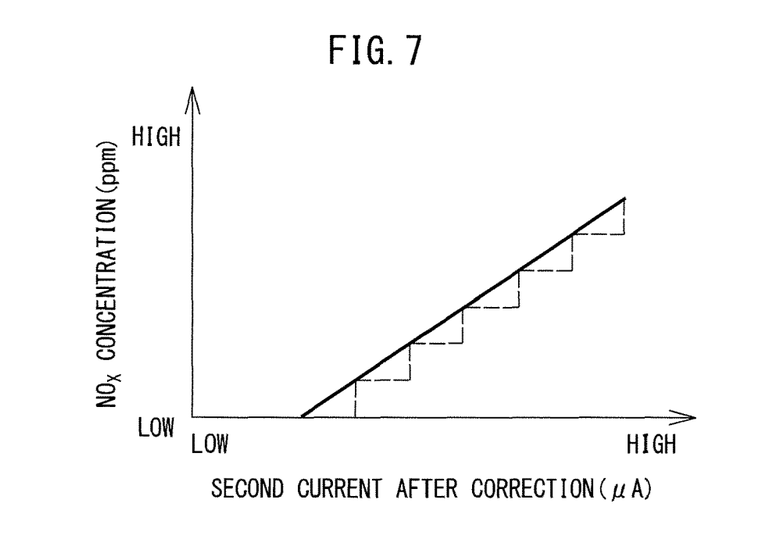
FIG. 7 is a map showing a relationship between a corrected second current and an $NO_X$ concentration in a measured gas.

The concentration calculating part 80a calculates the $NO_X$ concentration higher when the corrected second current I2*ac* is relatively high compared with when the corrected second current I2*ac* is relatively low. For example, the concentration calculating part 80a uses the map such as shown in FIG. 7 to calculate the $NO_X$ concentration. In this map, the $NO_X$ concentration is shown as a function of the corrected second current I2*ac*. Note that, the $NO_X$ concentration, as shown in FIG. 7 by the broken line, may be increased in stages (in steps) as the corrected second current I2*ac* becomes higher.

<Processing for Calculation of $NO_X$ Concentration>

Figure 8:
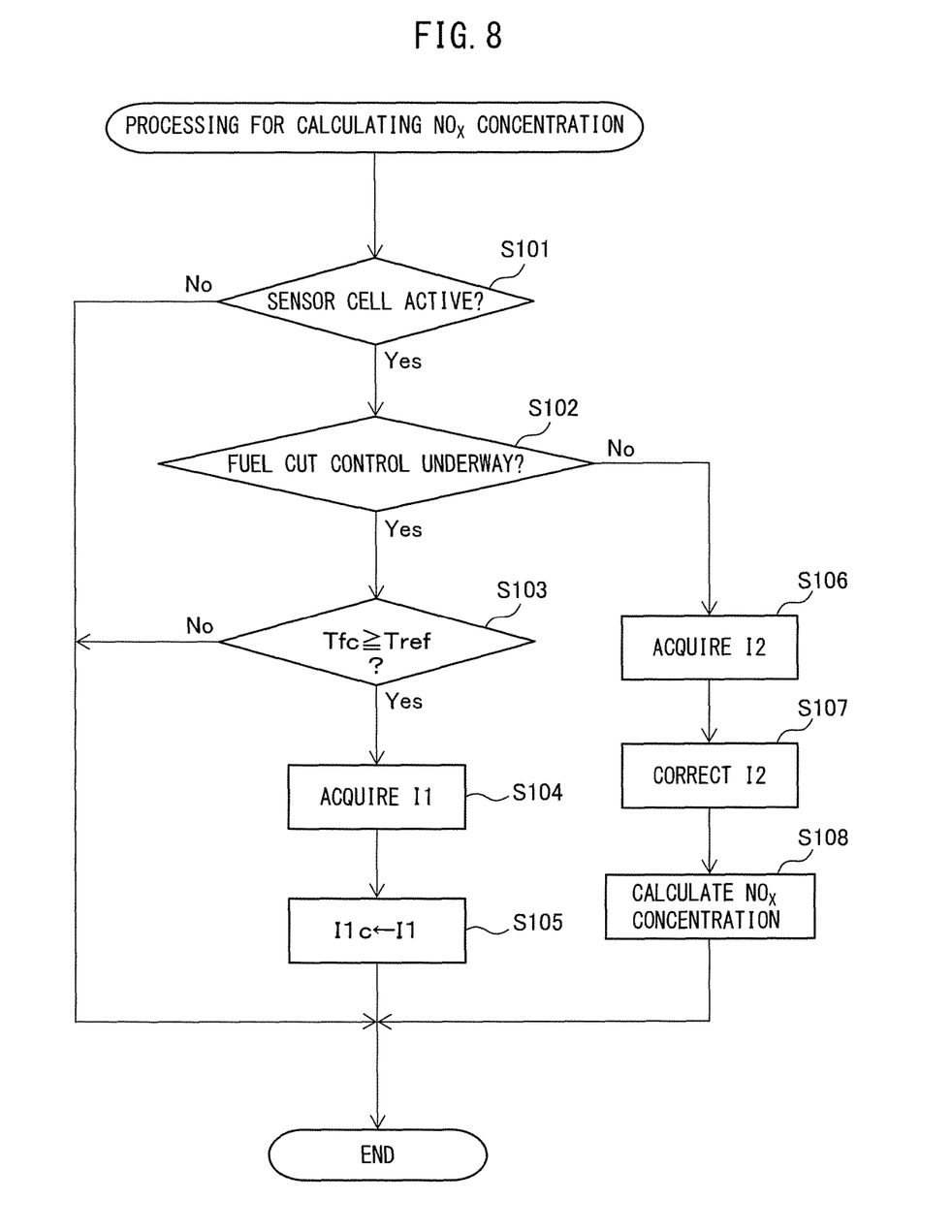
FIG. 8 is a flow chart showing a control routine of processing for calculating the $NO_X$ concentration in a first embodiment of the present invention.

Below, referring to the flow chart of FIG. 8, control for calculating the $NO_X$ concentration in the measured gas will be explained. FIG. 8 is a flow chart showing the control routine of processing for calculating the $NO_X$ concentration in the first embodiment of the present invention. The present control routine is repeatedly performed after the startup of the internal combustion engine 100 by the ECU 80 at predetermined time intervals.

First, at step S101, the concentration calculating part 80a judges whether the sensor cell 51 is in the active state. The concentration calculating part 80a judges that the sensor cell 51 is in the active state when the temperature of the sensor cell 51 is the activation temperature or more. On the other hand, the concentration calculating part 80a judges that the sensor cell 51 is not in the active state when the temperature of the sensor cell 51 is less than the activation temperature. The temperature of the sensor cell 51 is, for example, calculated based on the impedance of the sensor cell 51.

If at step S101 it is judged that the sensor cell 51 is not in the active state, the present control routine ends. On the other hand, if at step S101 it is judged that the sensor cell 51 is in the active state, the present control routine proceeds to step S102.

At step S102, the concentration calculating part 80a judges whether fuel cut control is being performed in the internal combustion engine 100. Note that, fuel cut control is started when a predetermined fuel cut start condition stands. For example, fuel cut control is performed when the amount of depression of the accelerator pedal 120 is zero or substantially zero (that is, the engine load is zero or substantially zero) and the engine speed is a predetermined speed higher than the speed at the time of idling or is more. Further, fuel cut control ends when a predetermined fuel cut end condition stands. For example, fuel cut control ends when the amount of depression of the accelerator pedal 120 becomes a predetermined value or more (that is, when the engine load becomes a predetermined value or more) or the engine speed becomes less than a predetermined speed higher than the speed at the time of idling.

If at step S102 it is judged that fuel cut control is being performed, the present control routine proceeds to step S103. At step S103, the concentration calculating part 80a judges whether the continuous execution time Tfc of the fuel cut control is a predetermined time Tref or more. The predetermined time Tref is at least the time required for the air to reach the measured gas chamber 30 of the sensor body 10 after fuel cut control is started and is determined in advance by experiments or calculations. The predetermined time is for example several seconds.

If at step S103 it is judged that the continuous execution time Tfc is a predetermined time Tref or more, the present control routine proceeds to step S104. In this case, it is guessed that air is introduced into the measured gas chamber 30 due to the fuel cut control. At step S104, the concentration calculating part 80a acquires the first current I1 detected by the current detection circuit 62 from the current detection circuit 62. Note that, after activation of the sensor cell 51, in order to detect the $NO_X$ concentration, a predetermined voltage is applied to the sensor cell 51 from the voltage application circuit 61. The predetermined voltage is for example a voltage of 1V or less.

Next, at step S105, the concentration calculating part 80a updates the current value I1*c* of the first current to the first current I1 acquired at step S104. The initial value of the current value I1*c* of the first current is, for example, the average value of the initial values of the first currents at the plurality of $NO_X$ sensors 1 and is determined in advance by experiments. The value of the current value I1*c* of the first current is stored in the RAM 83 of the ECU 80. After step S105, the present control routine is ended.

On the other hand, when at step S102 it is judged that fuel cut control is not being performed, the present control routine proceeds to step S106. In this case, normal control in which fuel is fed to the combustion chambers 2 is performed in the internal combustion engine 100. In the normal control, the amount of fuel depending on the operating state, etc., of the internal combustion engine 100 is fed to the combustion chambers 2. At step S106, the concentration calculating part 80a acquires the second current I2 detected by the current detection circuit 62 from the current detection circuit 62.

Next, at step S107, the concentration calculating part 80a corrects the second current I2 acquired at step S106 based on the ratio of the initial value of the first current and the current value I1*c* of the first current. Specifically, the second current I2 is corrected using the above formula (2). Next, at step S108, the concentration calculating part 80a calculates the $NO_X$ concentration in the measured gas based on the corrected second current I2*ac* calculated at step S107. The concentration calculating part 80a calculates the $NO_X$ concentration higher when the corrected second current I2*ac* is relatively high compared to when the corrected second current I2*ac* is relatively low. For example, the concentration calculating part 80a uses a map such as shown in FIG. 7 to calculate the $NO_X$ concentration. After step S108, the present control routine ends.

Note that, at step S105, the concentration calculating part 80a may use the following formula to update the current value of the first current I1c:

$$I1c=(I1cb \times n+I1)/(n+1) \quad (3)$$

where, I1cb is the current value of the first current before updating, I1 is the first current acquired at step S104, and "n" is an integer of 1 or more, for example, 3. By updating the current value I1c of the first current in this way, if the first current I1 detected by the current detection circuit 62 includes electrical noise, it is possible to reduce the effect of the noise on the current value I1c of the first current after updating. As a result, it is possible to more precisely estimate the degree of drop of the sensor output and in turn suppress more the drop in precision of detection of the $NO_X$ concentration.

Second Embodiment

The exhaust sensor according to the second embodiment is basically similar to the configuration and control of the exhaust sensor according to the first embodiment except for the points explained below. For this reason, below, the second embodiment of the present invention will be explained focusing on the parts different from the first embodiment.

The first electrode 41 differs individually in thickness, area, and number of active sites. For this reason, when the $NO_X$ sensor 1 is in its initial state, the output of the sensor cell 51 detected by the current detection circuit 62 will sometimes differ individually. For this reason, if making the initial value I1i of the first current in the above formula (2) the average value of the initial values of the first currents in a plurality of $NO_X$ sensors 1, it is liable to become impossible to precisely calculate the degree of drop from the initial value of the first current.

To deal with this issue, in the second embodiment, the initial value I1i of the first current in the above formula (2) is made the average value of the first currents detected first a predetermined number of times by the current detection circuit 62 after the $NO_X$ sensor 1 is mounted in the internal combustion engine 100. The predetermined number of times is an integer of 1 or more. The initial value I1i of the first current is stored in the ROM 82 of the ECU 80.

In the second embodiment, the initial values of the first currents detected at the same single piece are used to calculate the degree of drop from the initial value of the first current, so it is possible to precisely calculate the degree of drop from the initial value of the first current. As a result, it is possible to suppress more a drop in the precision of detection of the $NO_X$ concentration. Note that, in the second embodiment, in the same way as the first embodiment, the control routine for processing for calculation of the $NO_X$ concentration of FIG. 8 is performed.

Third Embodiment

The exhaust sensor according to the third embodiment is basically similar to the configuration and control of the exhaust sensor according to the first embodiment except for the points explained below. For this reason, below, the third embodiment of the present invention will be explained focusing on the parts different from the first embodiment.

As explained above, if making the initial value I1i of the first current in the above formula (2) the average value of the initial values of the first currents in a plurality of $NO_X$ sensors 1, it is liable to become impossible to precisely calculate the degree of drop from the initial value of the first current. Further, if determining the initial value of the first current like in the second embodiment, it is necessary to detect the initial value of the first current and write the detected initial value in the ROM 82 of the ECU 80 for each $NO_X$ sensor 1.

Further, as explained above, the $NO_X$ selectivity of the $NO_X$ sensor 1 does not substantially change due to deterioration of the $NO_X$ sensor 1 along with time, so the degree of drop of the first current and degree of drop of the second current due to the deterioration of the $NO_X$ sensor 1 along with the elapse of time become substantially equal. For this reason, the ratio of the first current and the second current does not substantially change due to deterioration of the $NO_X$ sensor 1 along with the elapse of time. Further, the ratio of the first current and the second current is correlated with the $NO_X$ concentration in the measured gas.

Therefore, in the third embodiment, the concentration calculating part 80a calculates the $NO_X$ concentration in measured gas based on the ratio of the first current and the second current. By doing this, it is possible to suppress a drop in the precision of detection of the $NO_X$ concentration due to a drop in the output of the sensor cell 51 caused by deterioration along with the elapse of time by a more simpler method.

Figure 9:
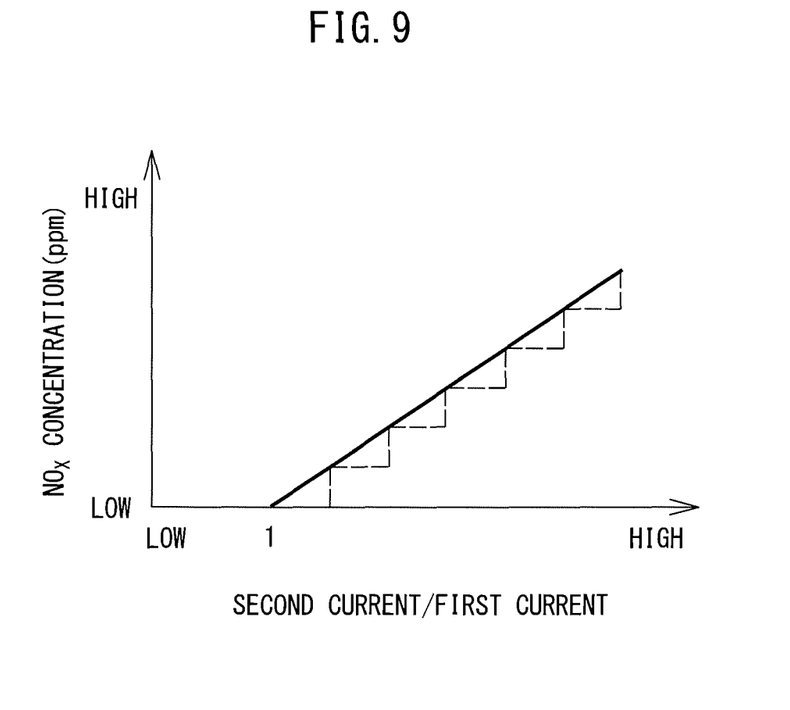
FIG. 9 is a view showing a relationship of a value of a second current divided by a first current and an $NO_X$ concentration in measured gas.

Specifically, the concentration calculating part 80a calculates the $NO_X$ concentration higher when the value of the second current divided by the first current is relatively large compared with when the value of the second current divided by the first current is relatively small. For example, the concentration calculating part 80a uses a map such as shown in FIG. 9 to calculate the $NO_X$ concentration. In this map, the $NO_X$ concentration is shown as a function of the value of the second current divided by the first current. Note that, the $NO_X$ concentration may be increased in stages (in steps) as shown in FIG. 9 by the broken line as the value of the second current divided by the first current becomes larger. Further, the concentration calculating part 80a may calculate the $NO_X$ concentration lower when the value of the first current divided by the second current is relatively large compared with when the value of the first current divided by the second current is relatively small.

<Processing for Calculation of $NO_X$ Concentration>

Figure 10:
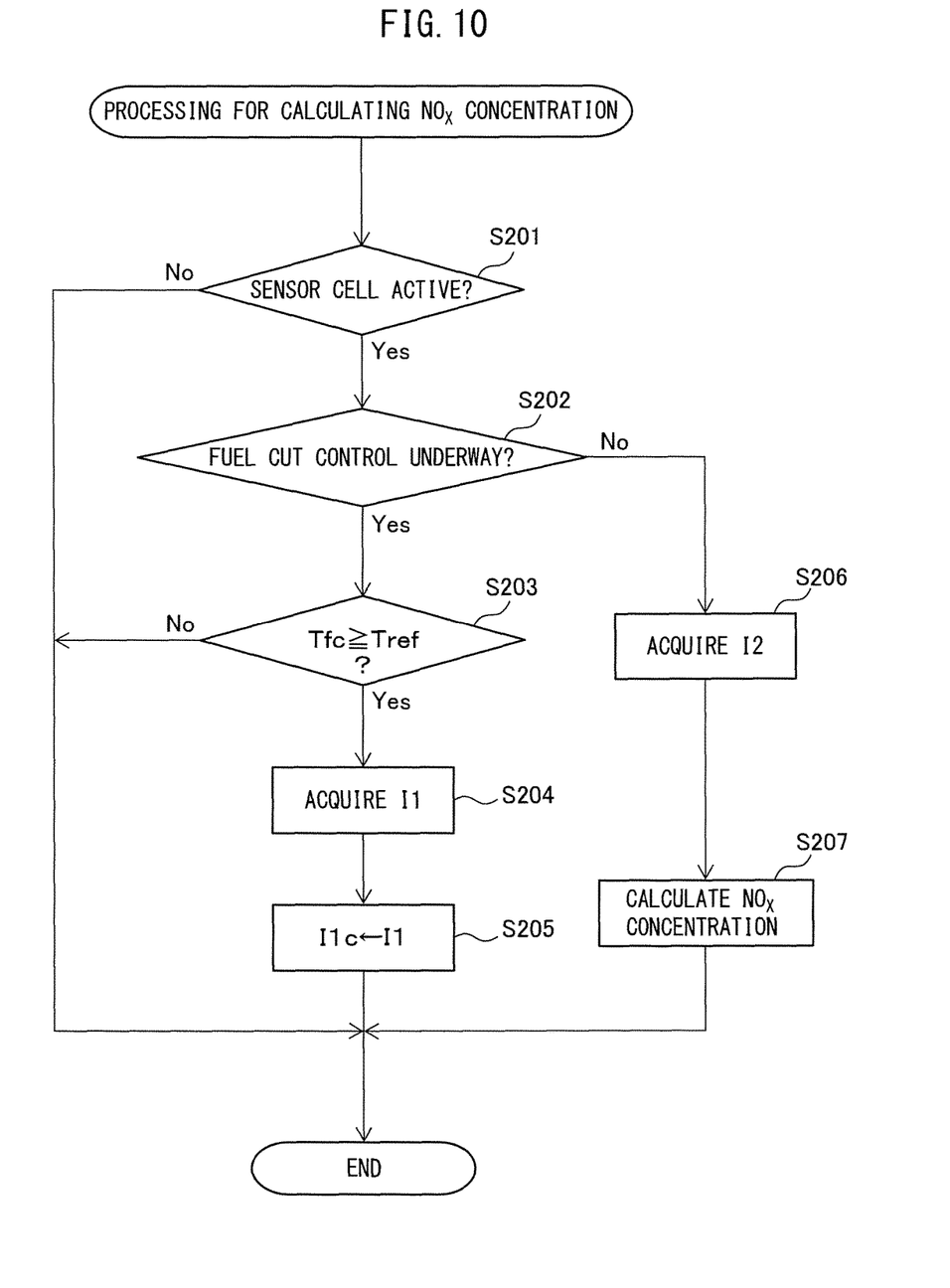
FIG. 10 is a flow chart showing a control routine of processing for calculating the $NO_X$ concentration in a third embodiment of the present invention.

Below, referring to the flow chart of FIG. 10, control for calculating the $NO_X$ concentration in the measured gas will be explained. FIG. 10 is a flow chart showing the control routine of the processing for calculating the $NO_X$ concentration in the third embodiment of the present invention. The present control routine is repeatedly performed after the startup of the internal combustion engine 100 by the ECU 80 at predetermined time intervals. Step S201 to step S206 in FIG. 10 are similar to step S101 to step S106 in FIG. 8, so explanations will be omitted.

After step S206, the present control routine proceeds to step S207. At step S207, the concentration calculating part 80a calculates the $NO_X$ concentration in the measured gas based on the ratio of the current value I1c of the first current updated at step 205 and the second current I2 acquired at step S206. The concentration calculating part 80a calculates the $NO_X$ concentration higher when the value of the second current I2 divided by the current value I1c of the first current is relatively large compared with when the value of the second current I2 divided by the current value I1c of the first current is relatively small. For example, the concentration calculating part 80a uses a map such as shown in FIG. 9 to calculate the $NO_X$ concentration. Note that, the concentration calculating part 80a may calculate the $NO_X$ concentration lower when the value of the current value I1c of the first current divided by the second current I2 is relatively large compared to when the value of the current value I1c of the first current divided by the second current I2 is relatively small. After step S207, the present control routine is ended.

Above, preferred embodiments according to the present invention were explained, but the present invention is not limited to these embodiments and can be corrected and changed in various ways within the scope of the claims. For example, the exhaust sensor may be a one-cell type ammonia sensor detecting a concentration of ammonia in exhaust gas. Note that, by using sensor elements similar to the above configuration and making the voltage applied to the sensor cell, the operating temperature of the sensor cell, etc., change, it is possible to selectively reduce and decompose ammonia in the presence of oxygen.

REFERENCE SIGNS LIST

1. $NO_X$ sensor (exhaust sensor)
2. combustion chamber
40. solid electrolyte layer
41. first electrode
42. second electrode
51. sensor cell
61. voltage application circuit
62. current detection circuit
80. electronic control unit (ECU)
80a. concentration calculating part
100. internal combustion engine

The invention claimed is:

1. An exhaust sensor detecting a concentration of a specific component in exhaust gas flowing through an exhaust passage of an internal combustion engine, comprising:
    a sensor cell having a solid electrolyte layer having an oxide ion conductivity, a first electrode arranged on one surface of the solid electrolyte layer so as to be exposed to the exhaust gas and comprised of a perovskite-type oxide, and a second electrode arranged on the other surface of the solid electrolyte layer so as to be exposed to a reference gas;
    a voltage application circuit applying voltage to the sensor cell so that a potential of the second electrode becomes higher than a potential of the first electrode,
    a current detection circuit detecting a current flowing through the sensor cell; and
    a concentration calculating part configured to calculate the concentration based on a current detected by the current detection circuit, wherein
    the current detection circuit detects a first current flowing through the sensor cell when fuel cut control where fuel stops being fed to combustion chambers of the internal combustion engine is being performed in the internal combustion engine and a predetermined voltage is applied from the voltage application circuit to the sensor cell, and detects a second current flowing through the sensor cell when normal control where fuel is being fed to the combustion chambers is being performed in the internal combustion engine and the predetermined voltage is applied from the voltage application circuit to the sensor cell, and
    the concentration calculating part is configured to calculate the concentration higher with respect to the second current when the first current is relatively low compared with when the first current is relatively high.

2. The exhaust sensor according to claim 1, wherein the concentration calculating part is configured to calculate the concentration based on a ratio of the first current and the second current.

3. The exhaust sensor according to claim 1, wherein the concentration calculating part is configured to correct the second current based on a ratio of an initial value of the first current and a current value of the first current and calculates the concentration based on the corrected second current.

4. The exhaust sensor according to claim 3, wherein the initial value of the first current is predetermined and is an average value of initial values of first currents at a plurality of the exhaust sensors.

5. The exhaust sensor according to claim 3, wherein the initial value of the first current is an average value of first currents first detected a predetermined number of times by the current detection circuit after the exhaust sensor is mounted in the internal combustion engine.

6. The exhaust sensor according to claim 1, wherein the exhaust sensor is a one-cell type nitrogen oxide sensor detecting a concentration of nitrogen oxide in exhaust gas.

7. The exhaust sensor according to claim 2, wherein the exhaust sensor is a one-cell type nitrogen oxide sensor detecting a concentration of nitrogen oxide in exhaust gas.

8. The exhaust sensor according to claim 3, wherein the exhaust sensor is a one-cell type nitrogen oxide sensor detecting a concentration of nitrogen oxide in exhaust gas.

9. The exhaust sensor according to claim 4, wherein the exhaust sensor is a one-cell type nitrogen oxide sensor detecting a concentration of nitrogen oxide in exhaust gas.

10. The exhaust sensor according to claim 5, wherein the exhaust sensor is a one-cell type nitrogen oxide sensor detecting a concentration of nitrogen oxide in exhaust gas.

* * * * *